US009237899B2

(12) United States Patent
Ray

(10) Patent No.: US 9,237,899 B2
(45) Date of Patent: Jan. 19, 2016

(54) TISSUE GRASPING FORCEPS AND LOCALIZING NEEDLE HOLDER

(76) Inventor: Stephen Paul Ray, Trevor, WI (US)

(*) Notice: Subject to any disclaimer, the term of this patent is extended or adjusted under 35 U.S.C. 154(b) by 629 days.

(21) Appl. No.: 12/958,861

(22) Filed: Dec. 2, 2010

(65) Prior Publication Data

US 2012/0143241 A1 Jun. 7, 2012

(51) Int. Cl.
*A61B 17/00* (2006.01)
*A61B 17/28* (2006.01)
*A61B 17/062* (2006.01)

(52) U.S. Cl.
CPC .............. *A61B 17/282* (2013.01); *A61B 17/062* (2013.01); *A61B 2017/00353* (2013.01); *A61B 2017/2837* (2013.01)

(58) Field of Classification Search
CPC ........... A61B 17/062; A61B 17/06161; A61B 17/28; A61B 17/282; A61B 17/0483; A61B 17/0469; A61B 2017/00353; A61B 2017/0411; A61B 2017/049; A61B 17/0467; A61B 17/04; A61B 17/06061; A61B 17/06; A61B 17/0625; A61B 17/285; A61B 17/29; A61B 17/2812; A61B 17/32; A61B 2017/1125; A61B 2017/320076; A61B 2017/320072; A61B 2017/2945; A61B 2017/22025; A61B 2017/22031; A61B 2017/2926; B25B 7/00; B25B 7/02
See application file for complete search history.

(56) References Cited

U.S. PATENT DOCUMENTS

| | | | |
|---|---|---|---|
| 2,583,892 | A | 1/1952 | Shellhouse |
| 3,083,711 | A | 4/1963 | Ramsay |
| 3,470,872 | A * | 10/1969 | Grieshaber ................ 600/217 |
| 3,489,151 | A | 1/1970 | Eller |
| 3,746,002 | A | 7/1973 | Haller |
| D246,190 | S | 10/1977 | Hodge |
| 5,059,214 | A | 10/1991 | Akopov |
| 5,188,636 | A * | 2/1993 | Fedotov ..................... 606/144 |
| 5,203,785 | A | 4/1993 | Slater |
| 6,077,280 | A * | 6/2000 | Fossum ...................... 606/151 |
| 6,106,542 | A * | 8/2000 | Toybin et al. .............. 606/205 |
| 6,315,780 | B1 | 11/2001 | Lalonde |
| 7,087,070 | B2 | 8/2006 | Flipo |
| 7,621,742 | B2 * | 11/2009 | Michaelson ................. 433/4 |
| 8,608,719 | B2 | 12/2013 | Ray |
| 8,617,130 | B2 | 12/2013 | Ray |
| 2004/0015181 | A1 * | 1/2004 | Sachatello et al. ......... 606/174 |
| 2009/0264897 | A1 * | 10/2009 | Wohl ........................ 606/110 |
| 2010/0145381 | A1 * | 6/2010 | Moon ........................ 606/207 |

(Continued)

FOREIGN PATENT DOCUMENTS

WO PCT/US2013/037714 4/2013

*Primary Examiner* — Jonathan W Miles
*Assistant Examiner* — Kendra Obu
(74) *Attorney, Agent, or Firm* — Lesavich High-Tech Law Group, S.C.

(57) ABSTRACT

A tissue grasping forceps and needle holder. A pair of movable arms are pivotably connected about a pivot connection, with each arm having a handle portion on one side and a working portion on the opposite side of the pivot connection. The working portions interengage when the handle portions are closed to a minimum spaced relation. The working portion has a clamp components and jaw component, with the clamp component comprising a plurality of synchronous teeth located to interlock when the handle portions are in the minimum spaced relation. The jaw component comprises a plurality of regularly spaced tines, with the tines being joined in pairs when the handle portions are in the minimum spaced relation with a gap between the tines, and an interstice between each spaced pair.

15 Claims, 6 Drawing Sheets

(56) References Cited

U.S. PATENT DOCUMENTS

2012/0143241 A1  6/2012  Ray
2013/0281961 A1  10/2013  Ray
2013/0296817 A1  11/2013  Ray

\* cited by examiner

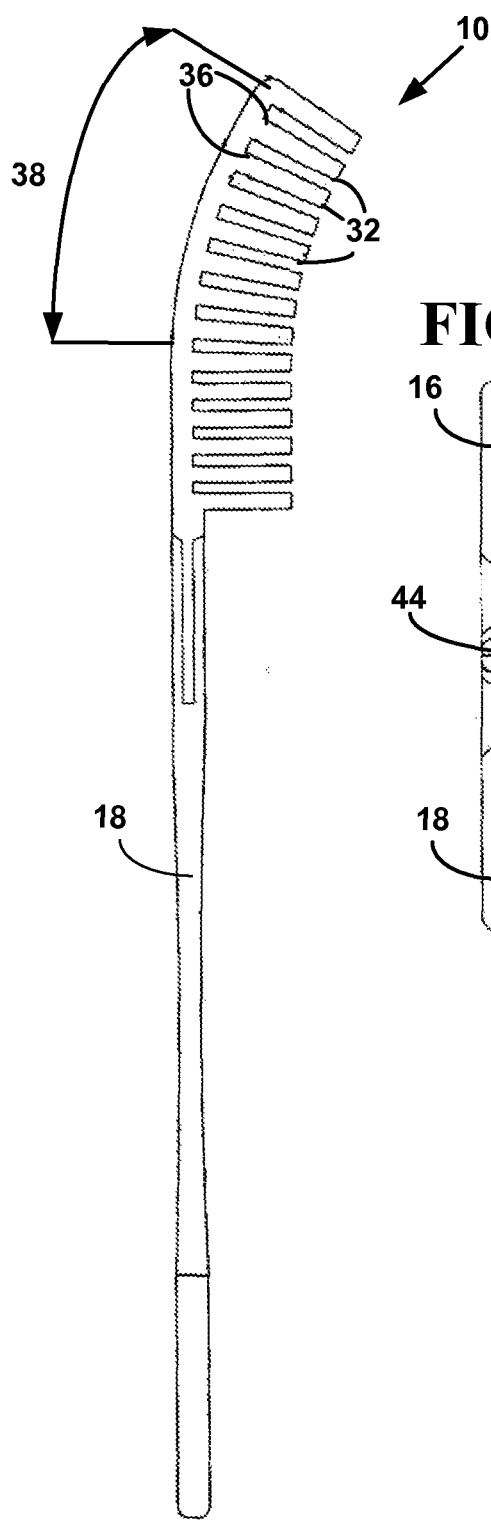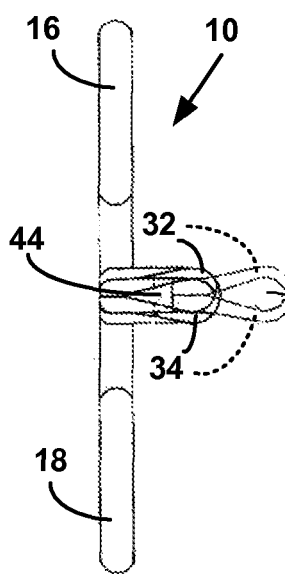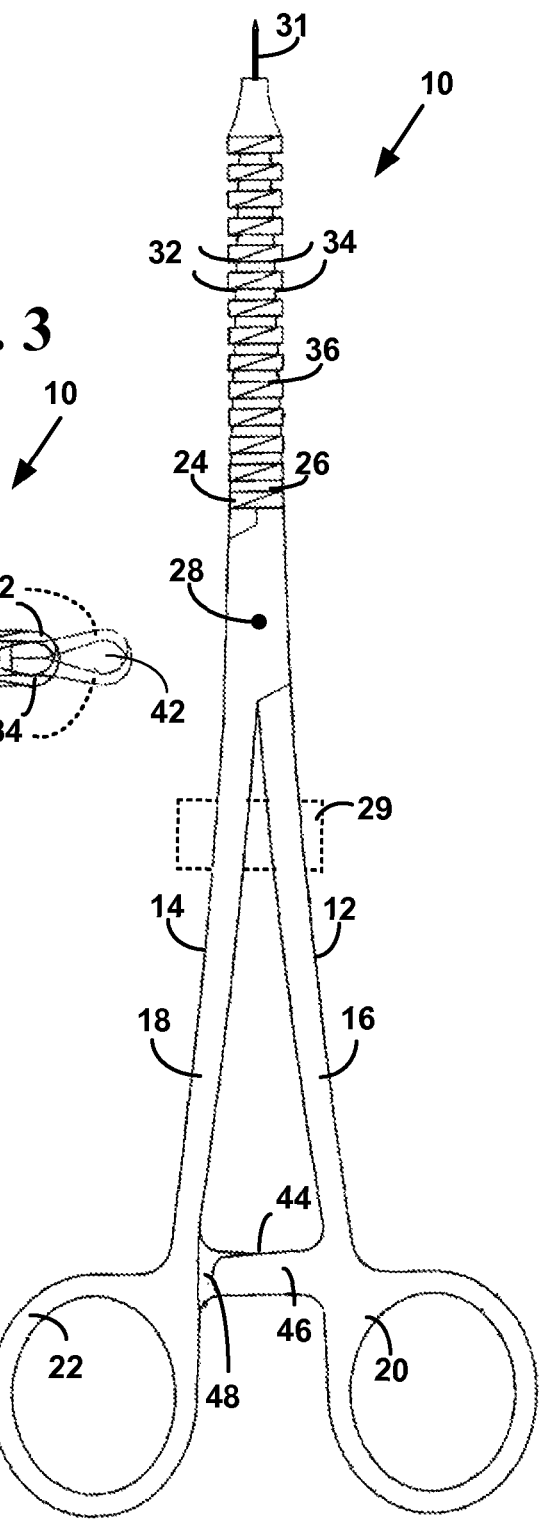

FIG. 4B
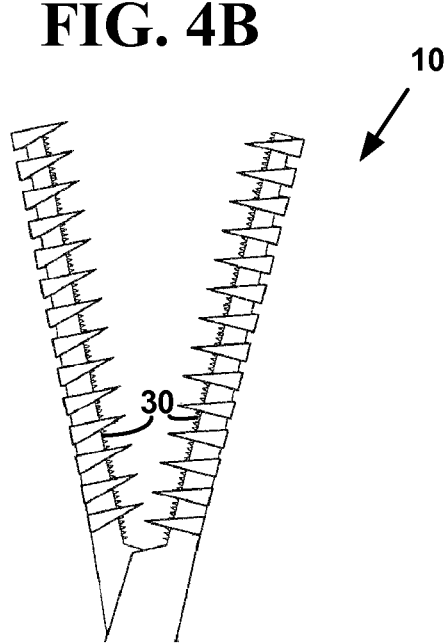
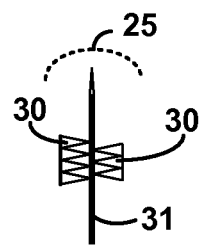

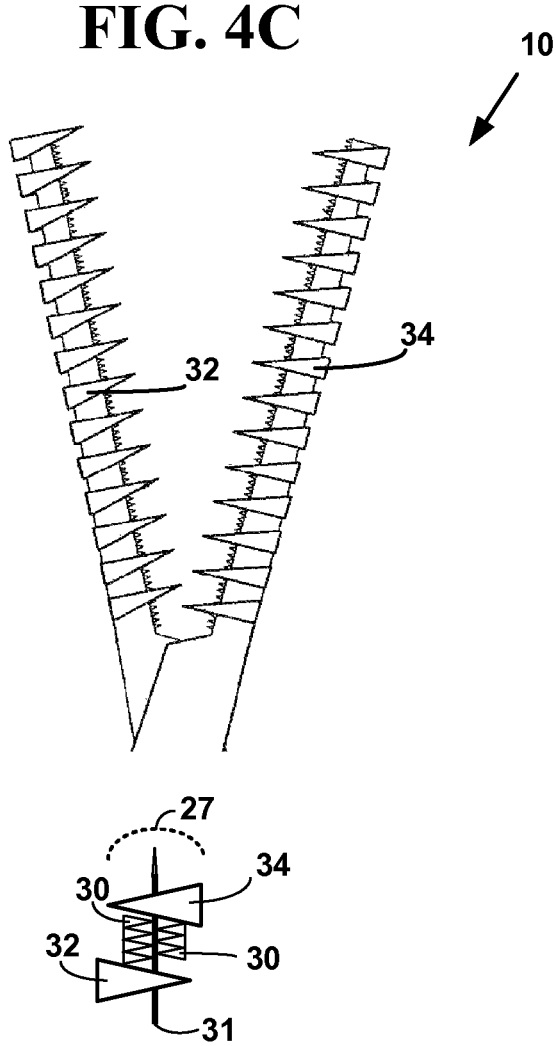

TISSUE GRASPING FORCEPS AND LOCALIZING NEEDLE HOLDER

BACKGROUND OF THE INVENTION

This invention relates to surgical instruments, and in particular to a single implement having a tissue grasping forceps and needle holder.

The grasping of a block of tissue to be removed during a surgical procedure can be difficult because the grasping forceps typically has only a single set of jaws, usually containing three teeth per jaw, and works best on surfaces parallel to the top of an operating table. When the surface is perpendicular or at an angle to the flat surface of the operating table, it is difficult to use such forceps because they do not grasp the surface easily. This makes it difficult to manipulate a block of tissue needing removal. Grasping of the tissue during the surgical procedure allows its manipulation and facilitates excision.

During certain procedures, such as breast lumpectomy surgery, localizing needles are used to locate a tumor. The amount of tissue around the tip of the needle needing removal is determined by the surgeon, and then a block of breast tissue is removed. During that removal, it is necessary to cut the needle where it protrudes from the skin and passes through the breast tissue. A length of needle, typically two to four centimeters, is left in tissue that is removed, and then is sent to a radiographer to make sure that the needle and tumor are removed adequately with a margin of healthy tissue surrounding the tumor. The cut end of the needle protrudes from the block of tissue to be removed, and during removal, the piece of needle remaining can be dislodged or moved during the excision process. There is currently no good way to secure the needle to the tissue at the angle and location achieved when the needle was placed.

SUMMARY OF THE INVENTION

The invention is directed to a tissue grasping forceps and needle holder. A pair of movable arms are pivotally connected about a pivot connection, with each arm having a handle portion with finger engaging openings, and each arm further having a working portion. The portions are located on opposite sides of the pivot connection. The working portions are shaped to interengage when the handle portions are in a minimum spaced relation, and disengage when the handle portions are spaced from the minimum spaced relation. Each working portion comprises a clamp component and a jaw component. Each clamp component comprises a plurality of synchronous teeth, with the teeth of clamp components being located to interlock when the handle portions are in the minimum spaced relation. Each jaw component comprises a plurality of regularly spaced tines, with the tines being located to join in spaced pairs when the handle portions are in the minimum spaced relation, with an interstice between each spaced pair.

In accordance with the preferred form of the invention, the clamp components face one another. Preferably, the teeth are serrated, interfitting when the handle portions are in the minimum spaced relation.

The arms lie generally in a plane, and each of the working portions includes a curved end section, with the curved end sections forming a concave tissue grasping segment extending from the plane. The tines of the jaw component extend generally normal to the plane.

Each of the spaced pair of tines includes a central gap. Each of the tines includes a curved tip culminating at a sharp point, with the curved tips of the spaced pair being complementary.

The handle portions includes a clasp. The clasp comprises a lug on each handle portion, with the lugs having interengageable ratchet teeth.

BRIEF DESCRIPTION OF THE DRAWINGS

The invention is described in greater detail in the following description of an example embodying the best mode of the invention, taken in conjunction with the drawing figures, in which:

FIG. 1 is a side elevational illustration of a tissue grasping forceps and needle holder according to the invention, FIG. 2 is an elevational view of the tissue grasping forceps and needle holder, looking from the right of FIG. 1, FIG. 3 is a bottom plan view of the grasping forceps and needle holder, taken from the bottom of FIG. 1 or FIG. 2, and showing, in phantom, the extent of the top pair of tines, FIG. 4B illustrates a portion of a clamp component open and closed and FIG. 4C illustrates a portion of jaw component opened and closed.

DESCRIPTION OF AN EXAMPLE EMBODYING THE BEST MODE OF THE INVENTION

Figure 4A:
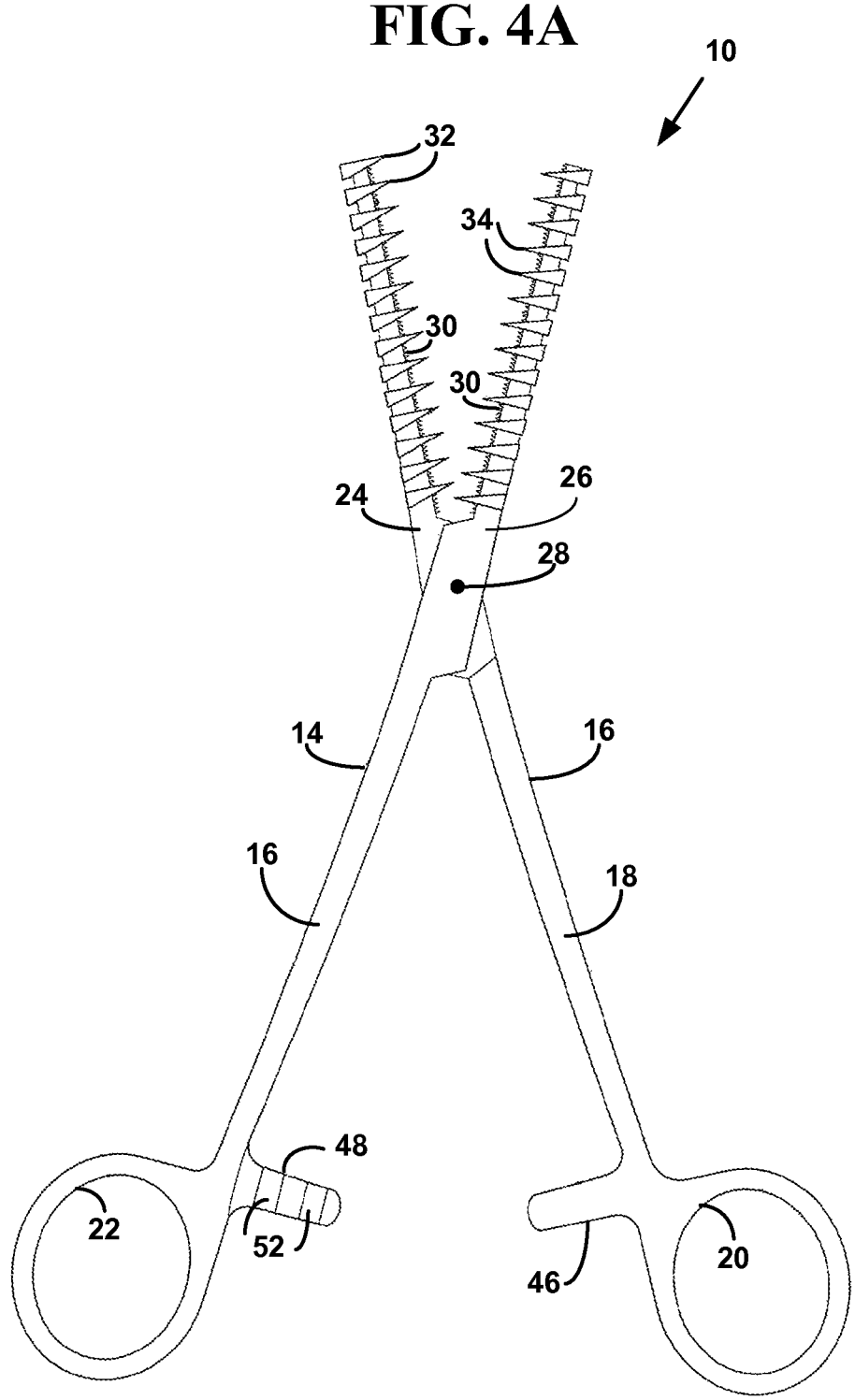
FIG. 4A is a view similar to FIG. 2, but with the handle portions and working portions opened.
Figure 5:
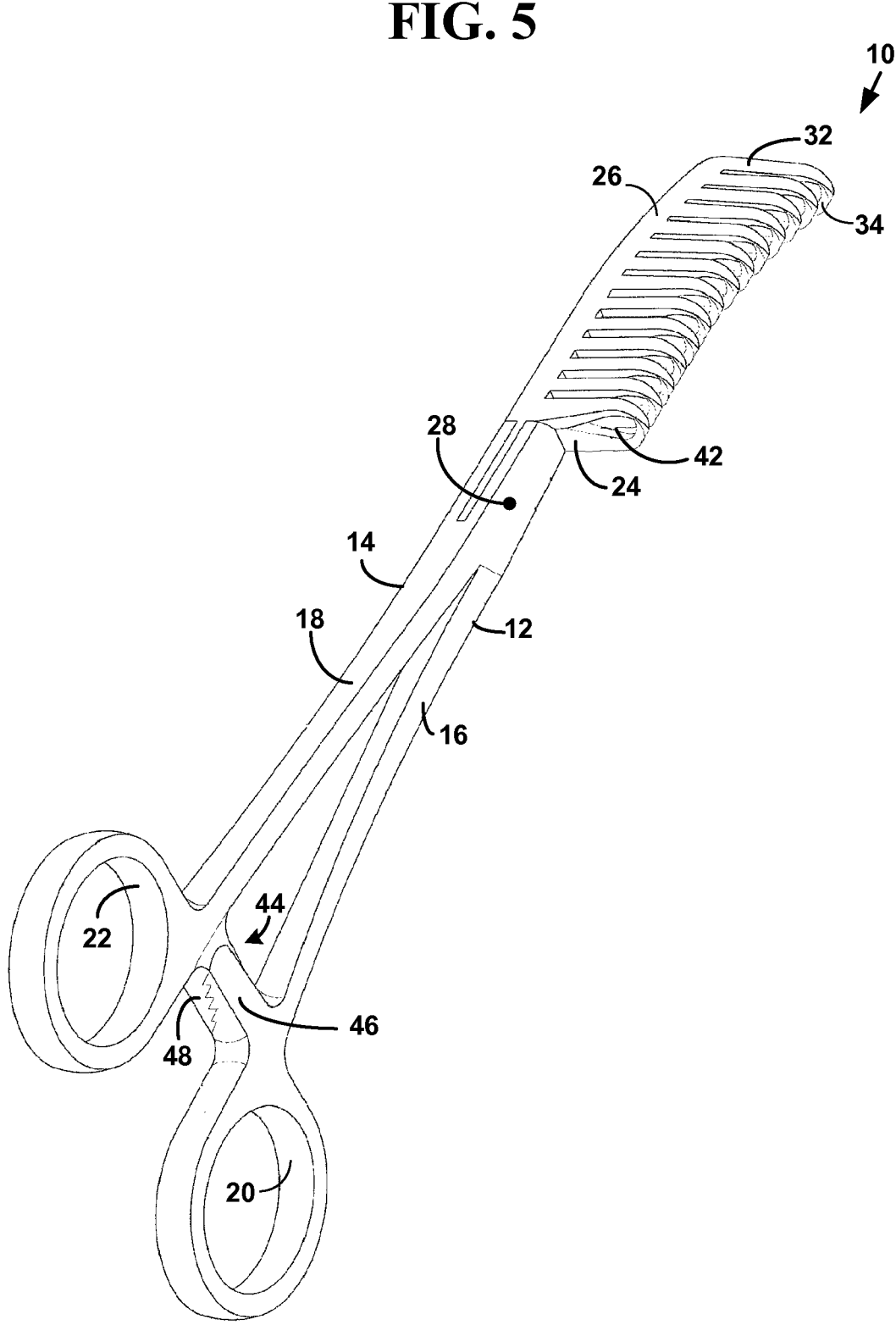
FIG. 5 is a perspective view of the tissue grasping forceps and needle holder, taken from the bottom left of FIG. 2.
Figure 6:
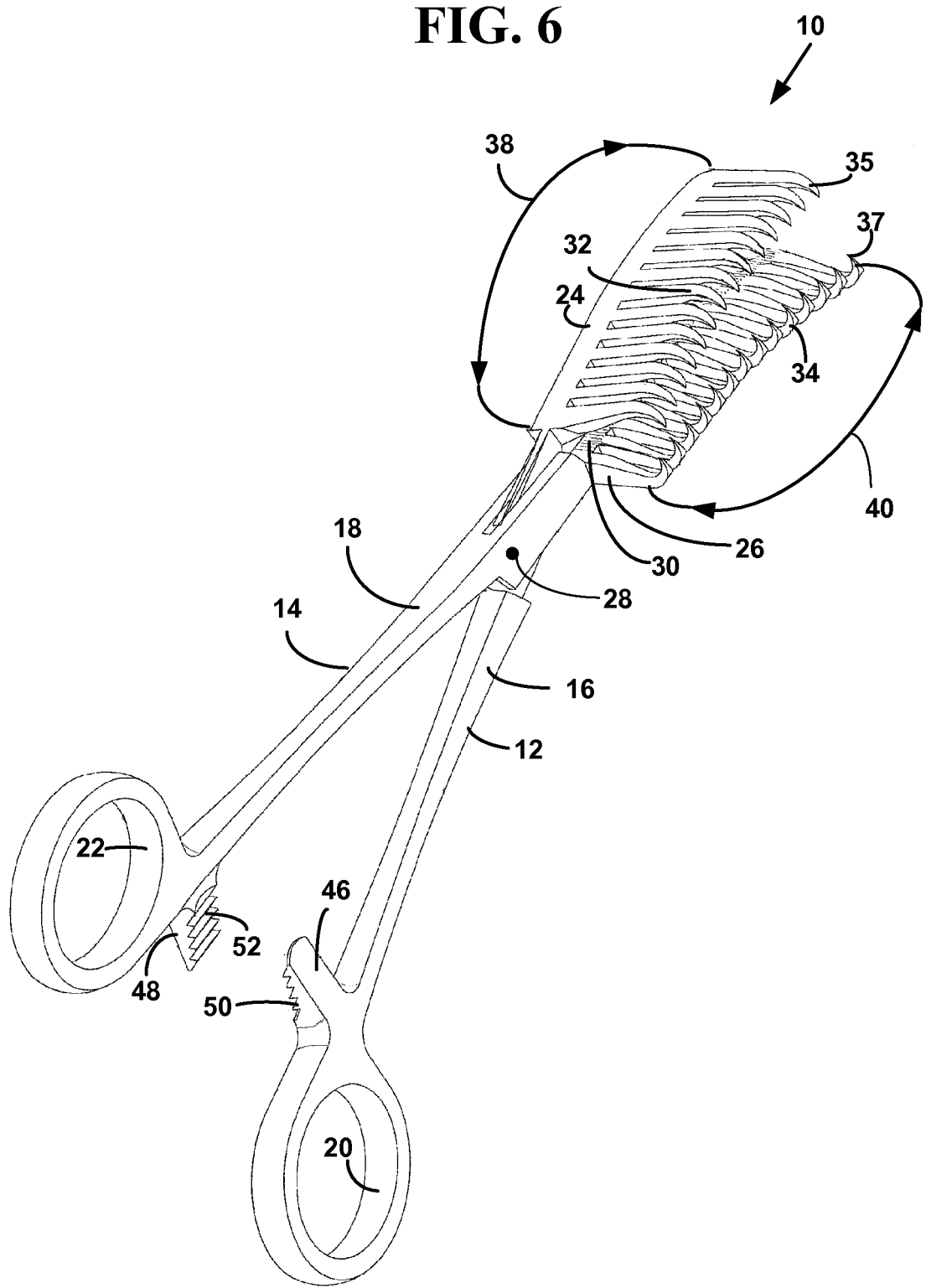
FIG. 6 is a view similar to FIG. 5, but with the handle portions and working portions opened.

A tissue grasping forceps and needle holder according to the invention is shown generally at 10 in the drawing figures. It comprises two primary components, a pair of movable arms 12 and 14, with each arm 12 and 14 having a respective handle portion 16 and 18. The respective handle portions 16 and 18 have finger engaging openings 20 and 22, as illustrated. Opposite ends of the arms 12 and 14 include respective working portions 24 and 26, with the handle portion and working portion of each arm being located on opposite sides of a pivot connection 28. The working portions 24 and 26 are shaped to interengage when the handle portions 16 and 18 are in a minimum spaced relation. That minimum spaced relation is best shown in FIGS. 2 and 5. The working portion 24 and 26 disengage when the handle portions 16 and 18 are spaced from the minimum spaced relation, as shown in FIGS. 4 and 6.

Each working portion 24 and 26 includes a clamp component and a jaw component. The clamp components comprises a plurality of synchronous teeth 30 on each of the working portions 24 and 26, the teeth 30 being located to interlock when the handle portions 16 and 18 are in the minimum spaced relation shown in FIGS. 2 and 5. As shown, the teeth 30, and thus the clamp components, face one another, and can therefore grasp and securely hold a needle when the tissue grasping forceps and needle holder 10 is used. Preferably the teeth 30 are serrated, therefore fitting closely together when the handle portions 16 and 18 are in the minimum spaced relation.

Each working portion 24 and 26 includes a clamp component 25 and a jaw component 27. The clamp components 25 comprises a plurality of synchronous teeth 30 on each of the working portions 24 and 26, the teeth 30 being located to interlock when the handle portions 16 and 18 are in the minimum spaced relation shown in FIGS. 2, 4B and 5. As shown, the teeth 30, and thus the clamp components 25, face one another, and can therefore grasp and securely hold a needle 31 when the tissue grasping forceps and needle holder 10 is used. Preferably the teeth 30 are serrated, therefore fitting closely together when the handle portions 16 and 18 are in the minimum spaced relation.

Each jaw component 27 comprises a plurality of regularly spaced tines 32 extending from the working portion 24 and tines 34 extending from the working portion 26. The tines 32 and 34 are appropriately located to be joined in pairs when the handle portions 16 and 18 are in the minimum spaced relation. The pairs are best shown in FIGS. 2, 4C and 5. An interstice 36 is formed between each of the spaced pairs of the tines 32 and 34.

As shown, the arms 12 and 14 lie generally in a plane 29. Each of the working portions 24 and 26 includes a respective curved end section 38 and 40, with the end sections forming a concave tissue grasping segment extending from the plane when the handle portions 16 and 18 are in the minimum spaced relation. The curved nature is best shown in FIGS. 1, 5 and 6. As shown, the tines 32 and 34 extend generally normal to the plane 29 of the arms 12 and 14.

As illustrated in the drawing figures, each of the tines 32 and 34 has a curved tip 35 culminating at a sharp point 37. When the arms 12 and 14 are closed to their minimum spaced relation, the tips, which are complementary to one another, interengage as best shown in FIGS. 2 and 3. When closed, a central gap 42 is formed between the tines 32 and 34 of each of the spaced pairs.

When the arms 12 and 14 are closed, engaging tissue to be excised, the tips of the tines 32 and 34 penetrate the tissue as the arms 12 and 14 are closed, and the central gaps 42 in each of the pair of tines 32 and 34, in combination with the interstices 36, form areas where the excised tissue is held firmly in place without damage. The removed tissue can then be biopsied or otherwise analyzed, as appropriate.

To maintain the arms 12 and 14 in a closed relationship, the tissue grasping forceps and needle holder 10 includes a clasp 44. The clasp 44 comprises a lug 46 on the handle portion 16 and a lug 48 on the handle portion 18. The lugs 46 and 48 each have respective interengageable ratchet teeth 50 and 52 for maintaining the arms 12 and 14 in the minimum spaced relation.

In use, the tissue grasping forceps and needle holder 10 is utilized by a surgeon during a surgical procedure, after tissue to be removed has been located and a needle 31 has been inserted in that tissue. The tissue grasping forceps and needle holder 10 are then closed on the tissue and the needle 31, with the needle being held in the teeth 30, and the tissue being grasped in the tines 32 and 34. The needle 31 is then cut, and the needle 31 portion in the tissue and the tissue itself, after excision, are then removed.

Various changes can be made to the invention without departing from the spirit thereof or scope of the following claims.

What is claimed is:

1. A tissue grasping forceps and needle holder, comprising:
    a pair of movable arms pivotally connected about a pivot connection, each arm having a handle portion with finger engaging openings, and each pair of movable arms further having a working portion, with said working and handle portions being located on opposite sides of said pivot connection;
    said pair of moveable arms lying generally in a plane, and each of said working portions includes a curved end section, said curved end sections forming a concave tissue grasping segment extending from said plane;
    said working portions being shaped to interengage when said handle portions are in a minimum spaced relation and to disengage when said handle portions are spread from said minimum spaced relation, each working portion simultaneously comprising both an internal clamp component and an external jaw component when in said minimum spaced relation;
    each internal clamp component comprising a plurality of synchronous teeth for grasping a localizing needle inserted in a tissue, said plurality of synchronous teeth of said internal clamp components being located to interlock and engage when said handle portions are in said minimum spaced relation;
    each external jaw component comprising a plurality of regularly spaced tines forming the concave tissue grasping segment of the curved end section for grasping the tissue around the localizing needle inserted into the tissue, said plurality of regularly spaced tines being located to join in spaced pairs when said handle portions are in said minimum spaced relation with an interstice between each spaced pair of tines, each of the tines having a curved tip culminating at a sharp point; and
    wherein simultaneously forming when said handle portions are in said minimum spaced relation, i) a localizing needle grasping component with the internal clamp component from the plurality of synchronous teeth of each internal clamp component interlocked and engaged for grasping the localizing needle inserted into the tissue and the external jaw components with the concave tissue grasping segment of the curved end section with the plurality of regularly spaced tines of each external jaw components joined with interstices between each joined pair of tines, ii) the concave tissue grasping segment adjacent to, parallel to, on an opposite side and about thereof, the localizing needle grasping component, and iii) central gaps in the plurality of regularly spaced tines in combination with the interstices in the concave tissue grasping segment forming concave areas of the curved end section where the tissue with the localizing needle inserted is held firmly in place without damage, and
    wherein the simultaneous forming of the localizing needle grasping component and the concave tissue grasping segment of the curved end section when said handle portions are in said minimum spaced relation thereby allowing both the tissue and the localizing needle inserted into the tissue to both be simultaneously grabbed and held and simultaneously and safely removed within the tissue grasping forceps and needle holder when the tissue is excised and the needle inserted into the tissue is cut during a surgery.

2. The tissue grasping forceps and needle holder according to claim 1, in which said internal clamp components face one another.

3. The tissue grasping forceps and needle holder according to claim 1, in which said plurality of synchronous teeth are serrated.

4. The tissue grasping forceps and needle holder according to claim 1, in which said plurality of regularly spaced tines extend generally normal to said plane.

5. The tissue grasping forceps and needle holder according to claim 1, in which each of said plurality of regularly spaced pairs of tines includes a central gap.

6. The tissue grasping forceps and needle holder according to claim 1, in which each of the plurality of regularly spaced tines includes the curved tip culminating at the sharp point, said curved tips of spaced pair being complementary.

7. The tissue grasping forceps and needle holder according to claim 1, including a clasp in said handle portion.

8. The tissue grasping forceps and needle holder according to claim 7, in which said clasp comprises a lug in each handle portion, said lugs having interengageable ratchet teeth.

9. A tissue grasping forceps and needle holder, comprising:
a pair of movable arms pivotally connected about a pivot connection, each pair of movable arms having a handle portion with finger engaging openings, and each arm further having a working portion, with said working and handle portions being located on opposite sides of said pivot connection;
said working portions being shaped to interengage when said handle portions are in a minimum spaced relation and to disengage when said handle portions are spread from said minimum spaced relation;
said pair of movable arms lying generally in a plane, and each of said working portions including a curved end section, said curved end sections forming a concave tissue grasping segment extending from said plane;
each working and handle portion comprising an internal clamp component and a an external jaw component,
each internal clamp component comprising a plurality of synchronous teeth for grasping a localizing needle inserted into a tissue, said plurality of synchronous teeth of said clamp components being located to interlock when said handle portions are in said minimum spaced relation;
each external jaw component comprising a plurality of regularly spaced tines forming the concave tissue grasping segment for grasping the tissue around the localizing needle inserted into the tissue, said plurality of regularly spaced tines being located to join in spaced pairs when said handle portions are in said minimum spaced relation with an interstice between each spaced pair;
each of the plurality of regularly spaced tines including a curved tip, said curved tips being complementary; and
wherein simultaneously forming when said handle portions are in said minimum spaced relation, i) a localizing needle grasping component with the internal clamp component from the plurality of synchronous teeth of each internal clamp component interlocked and engaged for grasping the localizing needle inserted into the tissue and the external jaw components with the concave tissue grasping segment of the curved end section with the plurality of regularly spaced tines of each external jaw components joined with interstices between each joined pair of tines, ii) the concave tissue grasping segment adjacent to, parallel to, on an opposite side and about thereof, the localizing needle grasping component, and iii) central gaps in the plurality of regularly spaced tines in combination with the interstices in the concave tissue grasping segment forming concave areas of the curved end section where the tissue with the localizing needle inserted is held firmly in place without damage, and
wherein the simultaneous forming of the localizing needle grasping component and the concave tissue grasping segment of the curved end section when said handle portions are in said minimum spaced relation thereby allowing both the tissue and the localizing needle inserted into the tissue to both be simultaneously held and simultaneously grabbed, held and safely removed within the tissue grasping forceps and needle holder when the tissue is excised and the needle inserted into the tissue is cut during a surgery.

10. The tissue grasping forceps and needle holder according to claim 9, in which said internal clamp components face one another.

11. The tissue grasping forceps and needle holder according to claim 9, in which said plurality of synchronous teeth are serrated.

12. The tissue grasping forceps and needle holder according to claim 9, in which said plurality of regularly spaced tines extend generally normal to said plane.

13. The tissue grasping forceps and needle holder according to claim 9, in which each of said plurality of regularly spaced pairs of tines includes a central gap.

14. The tissue grasping forceps and needle holder according to claim 9, including a clasp in said handle portion.

15. The tissue grasping forceps and needle holder according to claim 14, in which said clasp comprises a lug in each handle portion, said lugs having interengageable ratchet teeth.

\* \* \* \* \*